(12) United States Patent
Wright

(10) Patent No.: US 8,835,677 B2
(45) Date of Patent: Sep. 16, 2014

(54) METHODS FOR PRODUCING AMINONITROBENZOIC ACIDS

(75) Inventor: Christopher Wright, Arlington, MA (US)

(73) Assignee: Perkinelmer Health Sciences, Inc., Waltham, MA (US)

( * ) Notice: Subject to any disclaimer, the term of this patent is extended or adjusted under 35 U.S.C. 154(b) by 439 days.

(21) Appl. No.: 12/579,144

(22) Filed: Oct. 14, 2009

(65) Prior Publication Data

US 2010/0094046 A1 Apr. 15, 2010

Related U.S. Application Data

(60) Provisional application No. 61/105,225, filed on Oct. 14, 2008, provisional application No. 61/162,702, filed on Mar. 24, 2009.

(51) Int. Cl.
 C07C 205/00 (2006.01)
 C07C 207/00 (2006.01)
 C07C 227/04 (2006.01)

(52) U.S. Cl.
 CPC .................................. *C07C 227/04* (2013.01)
 USPC ........................................................ 562/437

(58) Field of Classification Search
 None
 See application file for complete search history.

(56) References Cited

PUBLICATIONS

Larsen et al. (J. Am. Chem. Soc., 1956, 78, 3210).*
Lei et al. (Huaxue Yanjiu Yu Yingyong, 2006, 18(3), 240).*
Google translation of excerpt from Lei et al. (Huaxue Yanjiu Yu Yingyong, 2006, 18(3), 240).*
English translation of excerpt from Lei et al. (Huaxue Yanjiu Yu Yingyong, 2006, 18(3), 240).*
Thomas, Gareth, J., "Herbicidal Activity of 6-Methylanthranilic Acid and Analogues", Journal of Agriculture Food Chemistry, American Chemical Society, 32, 1984, pp. 474-749.
Database Beilstein, Beilstein Institute for Organic Chemistry, Franfurt-Main, DE; 1901, XP002572826, downloaded Mar. 11, 2010.
Lloyd et al. "Intramolecular Hydrogen Bonding in ortho-Substituted Benzoic Acids". Journal of the American Chemical Society. Dec. 5, 1966.
Williams et al. "Determination of Positional Weighting Factors for the Swain and Lupton Substituent Constants F and R". Journal of the American Chemical Society. Jan. 21, 1976.
Porter, H.K. "The Zinin Reduction of Nitroarenes" Organic Reactions. pp. 455-459 (2004).

* cited by examiner

*Primary Examiner* — Rosalynd Keys
*Assistant Examiner* — Jennifer C Sawyer
(74) *Attorney, Agent, or Firm* — Lando & Anastasi, LLP

(57) ABSTRACT

Methods of producing aminonitrobenzoic acids are disclosed. A dinitrobenzoic acid may be reduced to an aminonitrobenzoic acid. In some specific embodiments, 2,6-initrobenzoic acid may be converted to 2-amino-6-nitrobenzoic acid. An end product may be used as an intermediate in the manufacture of various compounds including agricultural chemicals and pharmaceuticals.

16 Claims, 2 Drawing Sheets

METHODS FOR PRODUCING AMINONITROBENZOIC ACIDS

CROSS-REFERENCE TO RELATED APPLICATIONS

The present application claims priority under 35 U.S.C. §119(e) to U.S. Provisional Application Ser. No. 61/105,225, entitled "CHEMICAL SYNTHESIS METHODS AND RELATED COMPOUNDS" filed on Oct. 14, 2008, as well as to U.S. Provisional Application Ser. No. 61/162,702, entitled "METHOD FOR PRODUCING AMINONITROBENZOIC ACIDS" filed on Mar. 24, 2009, each of which is hereby incorporated herein by reference in its entirety for all purposes.

TECHNOLOGICAL FIELD

One or more aspects relate to methods for preparing aminonitrobenzoic acids by reduction of dinitrobenzoic acids.

BACKGROUND

Aminonitrobenzoic acid compounds are useful as building blocks in the manufacture of a variety of products including pharmaceuticals, agricultural chemicals, vitamins and dyes. The compound 2-amino-6-nitrobenzoic acid is a widely used type of aminonitrobenzene. Multiple methods for synthesizing this compound have been described in the literature. In one conventional approach, 2-amino-6-nitrobenzoic acid is prepared in a multi-step procedure starting from a 3-nitrophthalic anhydride precursor. (Journal of Organic Chemistry 63, 1998, 6797-6801). In another approach, 2-amino-6-nitrobenzoic acid is prepared from 2-chloro-6-nitrobenzoic acid by treatment with concentrated ammonia in a pressure vessel at elevated temperature in the presence of metallic copper as the catalyst (GB 286,694). The 2-chloro-6-nitrobenzoic acid used as the starting material can be prepared by a multi-step method from 2-chloro-6-nitrotoluene (U.S. Pat. No. 6,933,406).

SUMMARY

Aspects relate generally to methods for producing aminonitrobenzoic acids.

In accordance with one or more embodiments, a method for producing an aminonitrobenzoic acid may comprise reacting a dinitrobenzoic acid with a reducing agent under conditions sufficient to form an aminonitrobenzoic acid, wherein the reducing agent is selected from the group consisting of sulfide, hydrosulfide and polysulfide.

In some aspects, the reducing agent is sulfide. In other aspects, the reducing agent is hydrosulfide. In some aspects, the hydrosulfide is alkali metal hydrosulfide. In at least one aspect, the alkali metal is sodium. In other aspects, the reducing agent is polysulfide.

In some aspects, the dinitrobenzoic acid is 2,6-dinitrobenzoic acid. The reacting may be performed in a reaction mixture comprising one or more protic solvents. In one or more aspects, from about 1 to about 5 equivalents of reducing agent is used. In some aspects, the one or more protic solvent is selected from water and alcohol. The alcohol may be selected from methanol and ethanol. In some aspects, the reaction conditions comprise reflux temperature. The method may further comprise producing the dinitrobenzoic acid from dinitrotoluene.

In accordance with one or more embodiments, a reaction mixture may comprise a dinitrobenzoic acid, an aminonitrobenzoic acid, and a reducing agent selected from the group consisting of sulfide, hydrosulfide and polysulfide.

In some aspects, the aminonitrobenzoic acid comprises 2-amino-6-nitrobenzoic acid. The reaction mixture may further comprise one or more protic solvents.

In accordance with one or more embodiments, a batch method of producing an aminonitrobenzoic acid may comprise converting a dinitrobenzoic acid to the aminonitrobenzoic acid in a single step transformation.

In some aspects, the conversion is facilitated by a reducing agent selected from the group consisting of sulfide, hydrosulfide and polysulfide. In at least some aspects, the conversion is characterized by a yield of at least about 85%. In one or more aspects, the aminonitrobenzoic acid comprises 2-amino-6-nitrobenzoic acid.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF EXPLANATION OF THE DRAWINGS

Various aspects of at least one embodiment are discussed below with reference to the accompanying figures. The figures are provided for the purposes of illustration and explanation only and are not intended as a definition of the limits of the invention. In the figures.

DETAILED DESCRIPTION

Figure 1A:
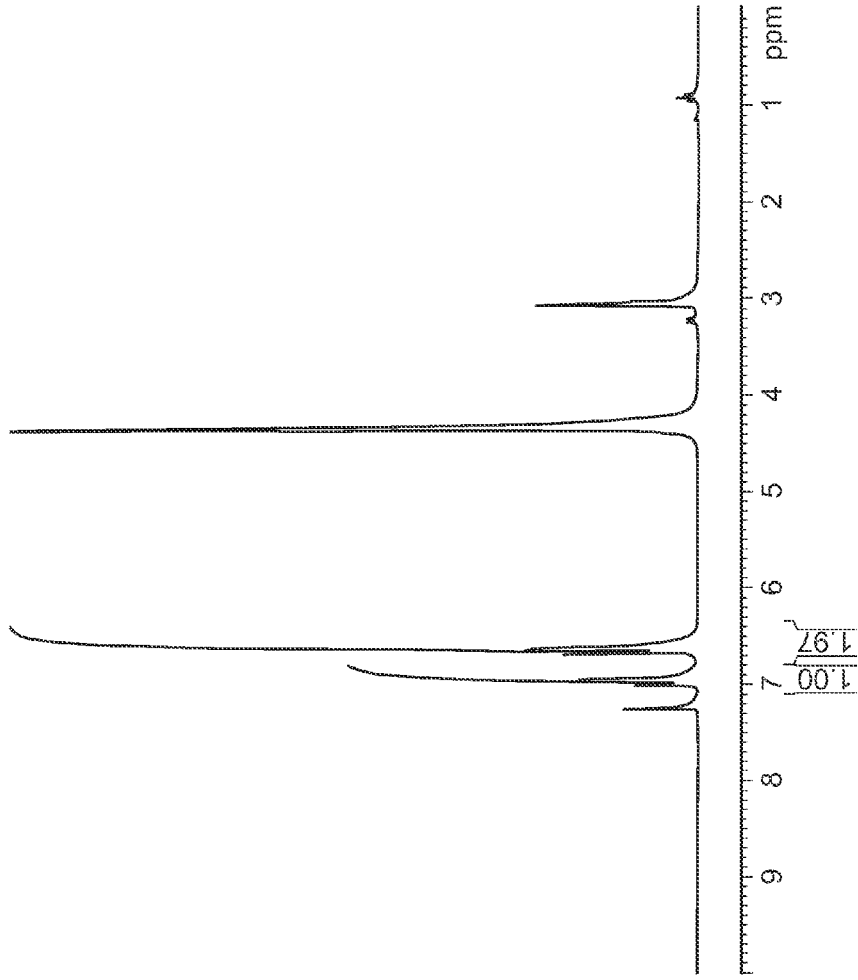
FIGS. 1a and 1b present data referenced in the accompanying Example.

In accordance with one or more embodiments, methods of producing aminonitrobenzoic acids are disclosed. In some embodiments, a dinitrobenzoic acid may be reduced to an aminonitrobenzoic acid. The disclosed reaction schemes involve relatively inexpensive and readily available reagents. The overall reaction chemistry is suitable for large scale synthesis and high yields are achievable. The end product may be useful, for example, in the synthesis of agricultural chemicals, imaging materials and pharmaceutical compounds.

In accordance with one or more embodiments, methods described herein involve using a dinitrobenzoic acid as a starting material for preparing an aminonitrobenzoic acid. As defined herein, the term "dinitrobenzoic acid" is a molecule including a benzoic acid moiety with nitro groups on both sides of the carboxylic acid group. Non-limiting exemplary dinitrobenzoic acids are 2,6-dinitrobenzoic acid, 1,3-dinitronaphthalene-2-carboxylic acid, 1,3-dinitro-1H-phenalene-2-carboxylic acid, 1,3-dinitroanthracene-2-carboxylic acid, 5,7-dinitroquinoline-6-carboxylic acid and 4-methyl-2,6-dinitrobenzoic acid.

In accordance with one or more embodiments, aminonitrobenzoic acids may be prepared by selective reduction of corresponding dinitrobenzoic acids such that a nitro group is reduced to an amino group. In at least one embodiment, dinitrobenzoic acids may be reduced to aminonitrobenzoic acids in a single step. In one specific non-limiting embodiment, 2,6-dinitrobenzoic acid may be converted to 2-amino-6-nitrobenzoic acid. Direct reduction of 2,6-dinitrobenzoic acid to 2-amino-6-nitrobenzoic acid has not been described although both of these compounds have been known for over a century, and methods for reducing one of two or three nitro groups of an aromatic ring are widely known. (March, J. Advanced Organic Chemistry 5th Ed, 1553, 2001).

In accordance with one or more embodiments, an approach for reducing dinitrobenzenes to aminonitrobenzenes is the Zinin reduction. (Organic Reactions, 20, 1973, 455-481). The term "Zinin reduction" may refer generally to a method for the reduction of nitroarenes by negative divalent sulfur, such as sulfide, hydrosulfide and polysulfides. Although not well-understood, the nature and positions of substituents of the aromatic ring appear to play an important role in the progress of this reaction. Thus, while Zinin reductions of 1,3-dinitrobenzenes to 1-amino-3-nitrobenzenes wherein the substituent between the nitro groups is either hydrogen or an electron-releasing group have been used, selective Zinin reductions of 1,3-dinitrobenzenes wherein the substituent between the nitro groups is an electron-withdrawing group have been considerably less successful. For example, treatment of 2-chloro-1,3-dinitrobenzene with hydrosulfide results not only in reduction of one of the nitro groups but also in dehalogenation. Notably, reduction of 3-methyl-2,6 dinitrobenzenesulfonic acid to 6-amino-3-methyl-2-nitrobenzenesulfonic acid by hydrosulfide has been reported but the yield was unsatisfactory. (Chemosphere, 38, 1999, 3119-3130). The use of the Zinin reduction for preparing 2-amino-6-nitrobenzoic acid has not been recognized.

In accordance with one or more embodiments, the dinitrobenzoic acid precursor may be produced from a starting material, such as a dinitrotoluene. In one non-limiting embodiment, 2,6-dinitrobenzoic acid may be produced from 2,6-dinitrotoluene. In at least some embodiments, 2,6-dinitrobenzoic acid may be produced from 2,6-dinitrotoluene using commonly known oxidation techniques commonly known in the art. (R. Warrener et al., Aust. J. Chem. 1980 33 277-9.)

In accordance with one or more embodiments, the reaction is performed in a solvent. Various solvents may be used but should generally promote solubility of the inorganic salts present in the reaction mixture. Associated boiling point may also be a consideration in selection of a solvent system. In various embodiments, a solvent system involving an alcohol and water may be used. In at least one embodiment, the solvent may be a protic solvent or mixtures thereof. Suitable protic solvents include, for example, water and alcohols such as methanol, ethanol, n-propanol and isopropanol. One non-limiting exemplary solvent mixture is methanol:water in various ratios, such as 9:5 (v/v). In other embodiments, aprotic solvents that mix with water may be used.

In accordance with one or more embodiments, a reducing agent is used to reduce a nitro group of a dinitrobenzoic acid to an amino group. Non-limiting exemplary reducing agents useful in the methods described herein may include ammonium sulfides, sodium sulfides, potassium sulfides, manganous sulfides, ferrous sulfides, hydrosulfides and polysulfides and mixtures thereof. In at least one embodiment, the reducing agent may be an alkali metal hydrosulfide, such as sodium hydrosulfide. The reducing agent may also include additives. In some embodiments, the reducing agent may include selenium.

Dinitrobenzoic acid may be reacted with a reducing agent under conditions sufficient to form an aminonitrobenzoic acid. In accordance with one or more embodiments, the reaction of dinitrobenzoic acid with a reducing agent may generally be carried out at reflux temperature. A range of temperatures may be used but it is generally important to avoid overheating. In some embodiments, a temperature in the range of about 60° C. to about 95° C. may be used. In at least one embodiment, the temperature may be at about 65° C. The reaction time implemented is generally dependent on various parameters including the reaction temperature, the amount of reducing agent used and the type of reducing agent used.

In accordance with one or more embodiments, a method may involve conversion of sodium sulfide to sodium hydrosulfide by, for example, sodium hydrogen carbonate. The method may also involve conversion of 2,6-dinitrobenzoic acid to its sodium salt by, for example, sodium hydrogen carbonate. This conversion may also bring about the solubilization of the 2,6-dinitrobenzoic acid. Other solubilizers commonly known in the art, such as sodium bicarbonate, may also be used. The sodium salt of 2,6-dinitrobenzoic acid may be converted (reduced) to the sodium salt of 2-amino-6-nitrobenzoic acid by a reducing agent, for example, the sodium hydrosulfide. The reduction reaction may proceed through one or more intermediates having various functional groups at the 2-position of the benzene ring, such as nitroso, hydroxylamino, azo and hydrazine. In at least some embodiments, only the aminonitrobenzoic acid and none of the intermediates are isolated.

In accordance with one or more non-limiting embodiments, the product aminonitrobenzoic acid, for example 2-amino-6-nitrobenzoic acid, may be isolated by a process involving steps such as evaporation of solvents, addition of water, washing of the aqueous solution with ether (ethereal washings discarded), acidification of aqueous solution, extraction with ether (aqueous solution discarded), drying of ethereal solution with anhydrous sodium sulfate, filtration of the ethereal solution, and evaporation of the ethereal solution to afford the desired product.

In accordance with one or more embodiments, the reactants may be present in any desired ratio. In some non-limiting embodiments, the ratio of sodium hydrogen carbonate to dinitrobenzoic acid may be about 1:1. In some non-limiting embodiments, from about 1 to about 5 equivalents of reducing agent may be used. For example, in at least one non-limiting embodiment, a ratio of reducing agent to dinitrobenzoic acid may be about 3:1. In at least one embodiment, product 2-amino-6-nitrobenzoic acid may be present after a reaction time of about 0.5 hours at a 3:1 ratio. A higher ratio may be associated with a faster reduction reaction rate. The potential for undesired reduction of the other nitro group should generally be taken into consideration when selecting various reaction parameters.

In accordance with one or more embodiments, dinitrobenzoic acid may be converted to aminonitrobenzoic acid in fewer than two steps. In some embodiments, a single step may be used to transform dinitrobenzoic acid to aminonitrobenzoic acid. In various embodiments, dinitrobenzoic acid may be converted to aminonitrobenzoic acid without isolating or purifying an intermediate. In at least one embodiment, dinitrobenzoic acid may be converted to aminonitrobenzoic acid in a one-pot reaction. In some embodiments, dinitrobenzoic acid may be converted to aminonitrobenzoic acid in a batch method.

In accordance with one or more embodiments, a reaction mixture may include dinitrobenzoic acid, a reducing agent and aminonitrobenzoic acid. In some embodiments, the reaction mixture may be substantially free of an anhydride. In at least one embodiment, the reaction mixture does not comprise an anhydride.

In one non-limiting reaction scheme, dinitrobenzoic acid may be reacted with about one to about five equivalents of an alkali hydrosulfide in a methanol:water mixture at reflux temperature for about 20 to about 40 minutes to produce an aminonitrobenzoic acid. As is described in the Example below, 2,6-dinitrobenzoic acid may be allowed to react with about three equivalents of sodium hydrosulfide in a methanol: water mixture at reflux temperature for about 30 minutes to produce 2-amino-6-nitrobenzoic acid. In some non-limiting embodiments, three equivalents of sodium hydrosulfide may be reacted with one equivalent of the sodium salt of 2,6-dinitrobenzoic acid in refluxing methanol/water followed by acidification.

In accordance with one or more embodiments, 2-amino-6-nitrobenzoic acid may be produced according to the overall reaction scheme illustrated below.

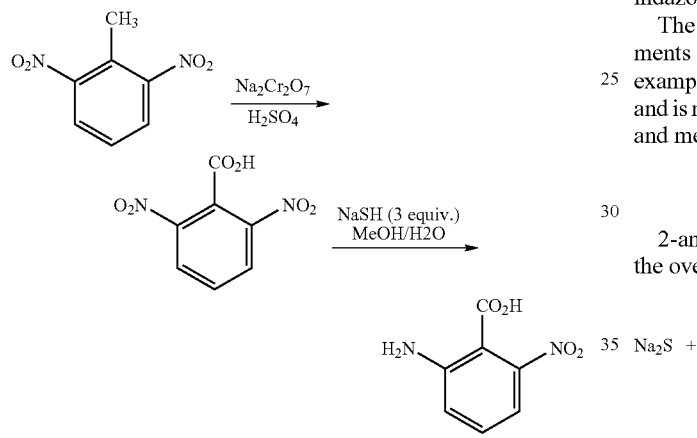

The first step may involve about a 50-60% yield of 2,6-dinitrobenzoic acid from 2,6-dinitrotoluene, for example, about 58% yield. The second step involving the reduction of 2,6-dinitrobenzoic acid may be characterized by a yield of at least about 80% of 2-amino-6-nitrobenzoic acid. In some embodiments, the yield of 2-amino-6-nitrobenzoic acid may be in a range of about 80% to about 95%. In various embodiments, the yield of 2-amino-6-nitrobenzoic acid may be at least about 85%. In some embodiments, the yield of 2-amino-6-nitrobenzoic acid may be at least about 90%. In at least one embodiment, the yield of 2-amino-6-nitrobenzoic acid may be about 93%. These yields may apply to various aminonitrobenzoic acids produced by the disclosed methods.

In accordance with one or more embodiments, a product aminonitrobenzoic acid, such as 2-amino-6-nitrobenzoic acid, may be used as an intermediate or building block material in the manufacture of various compounds including agricultural chemicals, imaging chemicals and pharmaceuticals. In at least one embodiment, methods of producing aminonitrobenzoic acid disclosed herein may be scaled-up and/or incorporated in larger processes for the manufacture of various desired end products. For example, a method of producing a desired pharmaceutical or agrochemical may include the disclosed steps of synthesizing an aminonitrobenzoic acid in addition to further steps of using the aminonitrobenzoic acid to produce the desired pharmaceutical or agrochemical. The disclosed methods may facilitate the production of various end products by offering cost reduction, efficiency and ease in terms of providing an aminonitrobenzoic acid as a building block.

In some embodiments, a polishing solution may be produced from aminonitrobenzoic acid, such as for use in chemical mechanical polishing techniques. In other embodiments, various agrochemicals including microbiocides and fungicides, such as amides and heterocyclic amide derivatives, may be prepared from aminonitrobenzoic acid. In still other embodiments, heterocyclic compounds useful for inhibiting blood clotting activity may be produced using aminonitrobenzoic acid. Disclosed aminonitrobenzoic acid may be used to produce pharmaceuticals directed at cancer treatment, including 5-substituted quinazolinone compounds and PLK inhibitors such as various pyrimidines. Pharmaceuticals directed to other conditions and disorders such as multiple sclerosis, asthma, allergic conditions, inflammatory and arthritic conditions, cardiovascular and cerebrovascular disorders may also be produced using aminonitrobenzoic acid. In some embodiments, such pharmaceuticals may include an indazole derivative produced using aminonitrobenzoic acid.

The function and advantages of these and other embodiments will be more fully understood from the following example. The example is intended to be illustrative in nature and is not to be considered as limiting the scope of the systems and methods discussed herein.

EXAMPLE 2-amino-6-nitrobenzoic acid was produced according to the overall reaction scheme illustrated below.

Na$_2$S +

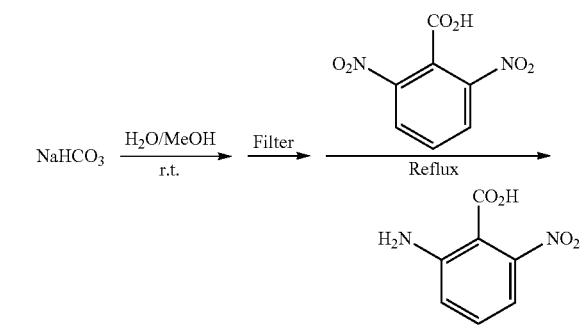

Sodium sulfide (1.50 mmol, 0.117 g) was dissolved in water (0.73 ml) in a 10 mL recovery flask with a magnetic stirbar. The solution was stirred in an ice bath and solid sodium hydrogen carbonate (1.50 mmol, 0.126 g) was added slowly. The ice bath was removed and the mixture was stirred for 20 minutes. Methanol (0.73 mL) was then added and a white precipitate formed. The mixture was stirred for 1.5 hours and then filtered without washing the precipitate.

In a separate recovery flask was placed 2,6-dinitrobenzoic acid (0.50 mmol, 0.106 g), methanol (0.95 mL) and water (0.2 mL). Sodium hydrogen carbonate (0.50 mmol) was added and the mixture was stirred at room temperature. After 10 minutes, the solution was almost clear and orange-red in color.

The mixture containing the 2,6-ditrobenzoic acid was stirred in an ice bath and the filtrate from above containing dissolved sodium hydrosulfide was added dropwise. The reaction mixture went deeper red. A reflux condenser with nitrogen balloon was fitted and the mixture was refluxed gently for 30 minutes. A very deep red mixture resulted.

A small sample was removed and the pH was adjusted to approximately 1 with dilute HCl. TLC co-spotted with standard (Silica GF, Hexane:Ether:Acetic Acid, 50:50:1, visualization by UV) showed mostly desired product. The reaction mixture was cooled to room temperature and worked up as follows. The mixture was evaporated to dryness. The solid residue obtained was taken up in a few mL of ether and water. (pH approximately 9.) The ether layer was discarded. The aqueous layer was acidified to pH 0.5. Sodium chloride was added to the aqueous solution to aid extraction of the product into ether. The aqueous solution was extracted with two 20 mL portions of ether. The combined ether extracts were dried over anhydrous sodium sulfate, filtered and evaporated to afford 0.0849 g (93% yield) of crude product.

Figure 1B:
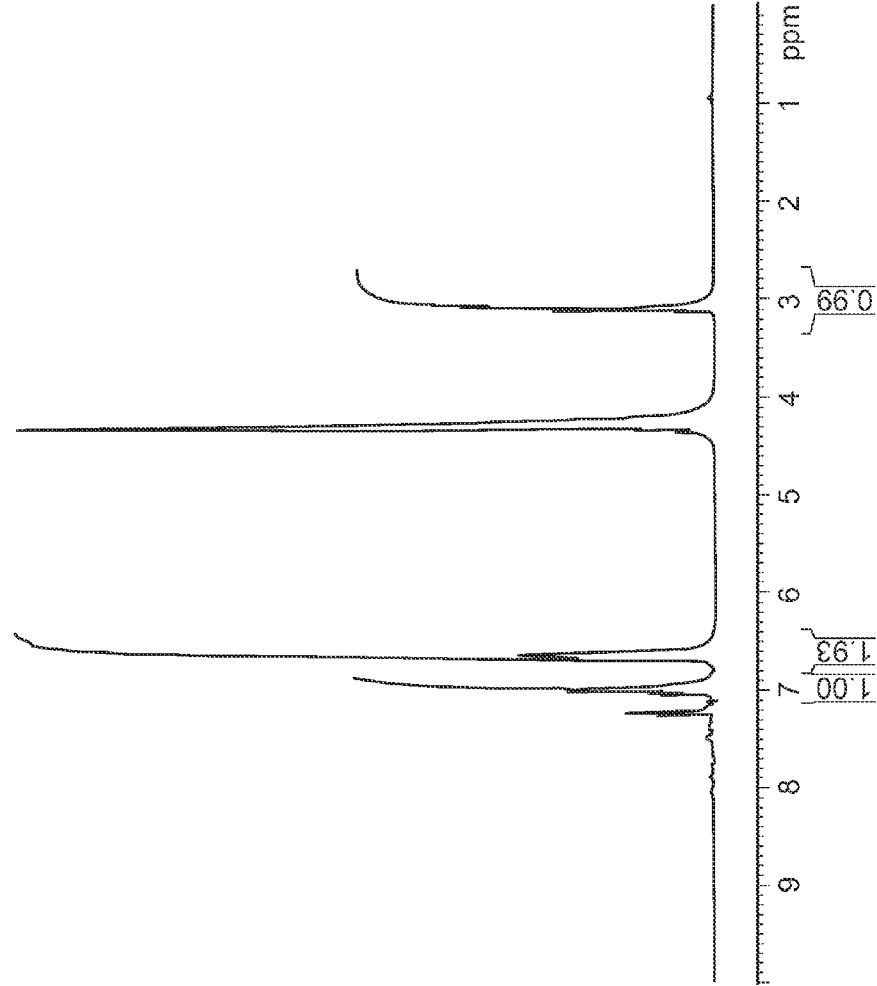

TLC co-spotted with standard (Silica GF, Hexane:Ether: Acetic Acid, 50:50:1, visualization by UV) showed almost entirely desired product 2-amino-6-nitrobenzoic acid. As illustrated by a comparison of FIGS. 1a and 1b, $^1$H NMR (300 mHz, $CD_3OD$) was identical to $^1$H NMR of a standard. A very small trace of ether was present in the synthesized material, but no other impurities were observed.

Having now described some illustrative embodiments and examples, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

It is to be appreciated that embodiments of the methods discussed herein are not limited in application to the details set forth in the following description or illustrated in the accompanying drawings. The methods are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

Moreover, it should also be appreciated that the invention is directed to each composition or method described herein and any combination of compositions or methods described herein and any combination of two or more compositions or methods, if such compositions or methods are not mutually inconsistent, is considered to be within the scope of the invention as embodied in the claims. Further, acts, elements, and features discussed only in connection with one embodiment are not intended to be excluded from a similar role in other embodiments.

The phraseology and terminology used herein is for the purpose of description and should not be regarded as limiting. The terms "comprising," "including," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims.

What is claimed is:

1. A method for producing 2-amino-6-nitrobenzoic acid, comprising:
    reacting 2,6-dinitrobenzoic-acid with a reducing agent under conditions sufficient to form 2-amino-6-nitrobenzoic acid in a reaction mixture comprising an alcohol and water in a ratio of about 9:5 (v/v) alcohol to water; and
    isolating 2-amino-6-nitrobenzoic acid from the reaction mixture,
    wherein the reducing agent is selected from the group consisting of sulfide, hydrosulfide and polysulfide.

2. The method according to claim 1, wherein the reducing agent is sulfide.

3. The method of claim 1, wherein the reducing agent is hydro sulfide.

4. The method of claim 1, wherein the reducing agent is polysulfide.

5. The method of claim 3, wherein the hydrosulfide is an alkali metal hydro sulfide.

6. The method of claim 5, wherein the alkali metal is sodium.

7. The method of claim 1, wherein the alcohol is selected from the group consisting of methanol, n-propanol, and iso-propanol.

8. The method of claim 7, wherein from about 1 to about 5 equivalents of reducing agent is used.

9. The method of claim 1, wherein the reaction conditions comprise reflux temperature.

10. The method of claim 1, further comprising producing the 2,6-dinitrobenzoic acid from dinitrotoluene.

11. A batch method of producing 2-amino-6-nitrobenzoic acid, comprising:
    converting 2,6-dinitrobenzoic acid to 2-amino-6-nitrobenzoic acid in a single step transformation performed in a reaction mixture comprising an alcohol and water in a ratio of about 9:5 (v/v) alcohol to water; and
    isolating the 2-amino-6-nitrobenzoic acid from the reaction mixture.

12. The batch method of claim 11, wherein the conversion is facilitated by a reducing agent selected from the group consisting of sulfide, hydrosulfide and polysulfide.

13. The batch method of claim 11, wherein the conversion is characterized by a yield of at least about 85%.

14. The method of claim 7, wherein the alcohol is methanol.

15. The batch method of claim 11, wherein the alcohol is methanol.

16. The method of claim 11, further comprising producing a pharmaceutical, agricultural chemical, vitamin or dye from the isolated 2-amino-6-nitrobenzoic acid.

\* \* \* \* \*

UNITED STATES PATENT AND TRADEMARK OFFICE
CERTIFICATE OF CORRECTION

PATENT NO. : 8,835,677 B2  Page 1 of 1
APPLICATION NO. : 12/579144
DATED : September 16, 2014
INVENTOR(S) : Christopher Wright It is certified that error appears in the above-identified patent and that said Letters Patent is hereby corrected as shown below:

On the title page, item 57, lines 3-4 Delete "2,6-initrobenzoic acid" and insert --2,6-dinitrobenzoic acid--

Signed and Sealed this
Seventeenth Day of May, 2016

Michelle K. Lee
*Director of the United States Patent and Trademark Office*